United States Patent
Langlois et al.

(10) Patent No.: US 10,156,548 B2
(45) Date of Patent: Dec. 18, 2018

(54) SYSTEM AND METHOD OF NON-DESTRUCTIVE INSPECTION WITH A VISUAL SCANNING GUIDE

(71) Applicants: Pierre Langlois, Quebec (CA); Benoit Lepage, Ancienne-Lorette (CA); Martin St-Laurent, Quebec (CA); Jason Habermehl, Quebec (CA)

(72) Inventors: Pierre Langlois, Quebec (CA); Benoit Lepage, Ancienne-Lorette (CA); Martin St-Laurent, Quebec (CA); Jason Habermehl, Quebec (CA)

(73) Assignee: Olympus Scientific Solutions Americas Inc.

( * ) Notice: Subject to any disclaimer, the term of this patent is extended or adjusted under 35 U.S.C. 154(b) by 806 days.

(21) Appl. No.: 13/955,399

(22) Filed: Jul. 31, 2013

(65) Prior Publication Data

US 2015/0039245 A1   Feb. 5, 2015

(51) Int. Cl.
*G01N 29/24* (2006.01)
*G01N 29/04* (2006.01)
*G01N 29/22* (2006.01)
*G01N 29/26* (2006.01)
*G01N 27/90* (2006.01)

(52) U.S. Cl.
CPC ......... *G01N 29/043* (2013.01); *G01N 29/225* (2013.01); *G01N 29/262* (2013.01); *G01N 27/902* (2013.01); *G01N 29/24* (2013.01); *G01N 2291/267* (2013.01); *G01N 2291/2638* (2013.01)

(58) Field of Classification Search
USPC .......................................... 702/39
See application file for complete search history.

(56) References Cited

U.S. PATENT DOCUMENTS

| | | | | |
|---|---|---|---|---|
| 6,573,712 B2 * | 6/2003 | Arai | ................... | G01N 27/9053 324/225 |
| 9,250,213 B1 * | 2/2016 | Bossi | ................... | G01N 29/265 |
| 2004/0019303 A1 * | 1/2004 | Thomson | ............... | A61B 5/103 600/595 |
| 2005/0123171 A1 * | 6/2005 | Kobayashi | .............. | G06F 3/011 382/103 |

(Continued)

FOREIGN PATENT DOCUMENTS

WO   WO 2009083674 A1 *   7/2009   ............. G01B 21/04

*Primary Examiner* — Paul D Lee
(74) *Attorney, Agent, or Firm* — C. Tricia Liu (57) ABSTRACT

Disclosed is an inspection device and method of guiding an inspection probe according to a predetermined inspection plan. The device is couple with a probe which is to be moved according to the inspection plan on the test object, the device including an inspection guide unit having a guide control unit, a position encoding such as a 3-D camera and visual feedback eyewear. The method including facilitating a virtual display of the inspection plan onto the visual feedback eyewear, moving the probe following the virtual display of the inspection plan, sensing sensed probe positions in real time of the inspection using the 3-D camera and validating the sensed probe position against the inspection plan using the control module. Then the information of the step of validating, such as those spots at which the probe is moved out of the tolerance of the inspection plan, is displayed on the feedback eyewear.

23 Claims, 5 Drawing Sheets

(56) References Cited

U.S. PATENT DOCUMENTS

| | | | | |
|---|---|---|---|---|
| 2007/0282543 | A1* | 12/2007 | Hiyama | G01N 29/06 702/39 |
| 2008/0048879 | A1* | 2/2008 | Lipman | B60K 37/02 340/688 |
| 2010/0305876 | A1* | 12/2010 | Lee | G01B 21/20 702/38 |
| 2011/0025316 | A1* | 2/2011 | Faucher | G01N 27/9026 324/240 |
| 2012/0320372 | A1* | 12/2012 | Troy | B64F 5/0045 356/237.2 |
| 2013/0237822 | A1* | 9/2013 | Gross | A61B 8/13 600/439 |
| 2014/0207419 | A1* | 7/2014 | Messinger | G01N 27/90 703/1 |

\* cited by examiner

SYSTEM AND METHOD OF NON-DESTRUCTIVE INSPECTION WITH A VISUAL SCANNING GUIDE

FIELD OF THE INVENTION

The present disclosure generally relates to a method and a system for conducting non-destructive testing/inspection (later as NDT/NDI), and more particular, it relates to guiding and informing an inspector in real time of an inspection path during a manual inspection of a test object.

BACKGROUND OF THE INVENTION

Inspection of complex parts by non-destructive technologies can be quite challenging as finding and sizing a flaw or defect heavily depends on probe positioning during inspection. In the exemplary embodiment of this invention, a nozzle weld phased array ultrasonic (PAUT) inspection is used. The exact position and number of required PAUT scan lines on particular nozzle geometry is defined by the scan plan, knowing that for weld inspection the whole weld zone must typically be completely covered by the various PAUT beams. The complex shape of the nozzle, defined by the intersection of two cylinders, makes it difficult to follow the inspection scan line to ensure correct coverage of the inspected weld as defined by the scan plan.

The conventional way of conducting PAUT nozzle inspection is manually, with or without a guide on the part. The user must be experienced as he needs to compensate for the effects of the geometry on the ultrasound signal path in order to achieve the interpretation of the scan result. Because such an inspection relies heavily on the user's experience, reproducibility and reliability is poor. Under those conditions, it is also impossible to ensure the complete part was covered and to save meaningful data as the real position of the probe is unknown to the inspection system.

A more robust way of inspecting a nozzle is to use an automated scanner, specific to the nozzle geometry, which encodes all PAUT probe movement and ensures coverage by precisely positioning the probe on the inspected part surface. Such a scanner is an expensive alternative and is not suitable for all markets. It also takes a lot of time to deploy, install and it lacks the manual versatility to better size a flaw or defect.

Either solution requires having a scan plan which is calculated depending on measured parameters of the nozzle such as radius, thickness, pipe thickness and pipe radius.

Advances in technologies now permit a probe to locate an object with very good precision without the use of a specific scanner. In the preferred embodiment, the chosen encoding unit is a 3D camera that uses two specific objectives to locate a moving target, which reflects infrared, using the stereoscopy principle. Attempts have been made to use such advanced encoder systems for the manual inspection of complex geometries such as the nozzle. While these attempts solved some of the limitations of manual inspection (such as traceability and analysis) it has not been devised as an effective tool for guiding the probe position during the inspection.

It would be desirable to have a way of using the advanced encoding unit, a 3D camera, to provide adequate feedback of the scanning path during the inspection in order to significantly increase the accuracy and efficiency manual inspection.

SUMMARY OF THE INVENTION

Disclosed is a visual scanning guide system and method for guiding a scan path of a manual NDT/NDI process as it inspects flaws along a predetermined inspection line. In the exemplary embodiment, the guide system assists the inspection of a nozzle to pipe weld using a PA Ultrasound technique. Preferably by using an existing automated wizard with known geometric parameters of the pipe and nozzle, configuration information regarding a desirable path to scan the weld in order to have full coverage is provided. The configuration information also includes operational parameters such as the beam formation to use, which part of the signal is meaningful (gating), what scan line to follow and the number of passes that are necessary to have a full coverage. An acquisition unit of the PA system is configured according to the parameters above and is ready to inspect.

The visual scan guide system embodies a position encoding unit which is preferably a 3D camera to report real time position and orientation of the probe. Also embodied is a pair of Referenced Feedback glasses, which is partially see-through and partially a screen that can display images generated by a scan path control module. The glasses is configured to display part of the configuration information, such as the desired scanning path, and to allow wearers or inspectors to see through to observe where the probe's location is in relationship to the desired scanning path. As the inspection continues, the user is informed on the screen of the glasses with information from the scan path control module, including a bad position of the probe, the lack of coupling fluid and the found flaw or defect position. If the probe capability permits it, the system compensates for small positioning errors by modifying the beam formation to alleviate the error. Since only meaningful data is saved, the analysis of the resulting data is simplified and a proper coverage of the weld can be proven.

The novel aspects of the present invention can be summarized as to include,

The integration of an automatically calculated scan plan, a position encoding unit and a visual feedback unit (the glasses) to provide real time information guiding the user to follow the planned scan path;

The usage of an encoding unit (a 3D camera is exemplarily used) to dynamically correct the focal laws in order to maintain a detection capability as defined in a scan plan.

DETAILED DESCRIPTION OF THE INVENTION

Figure 1:
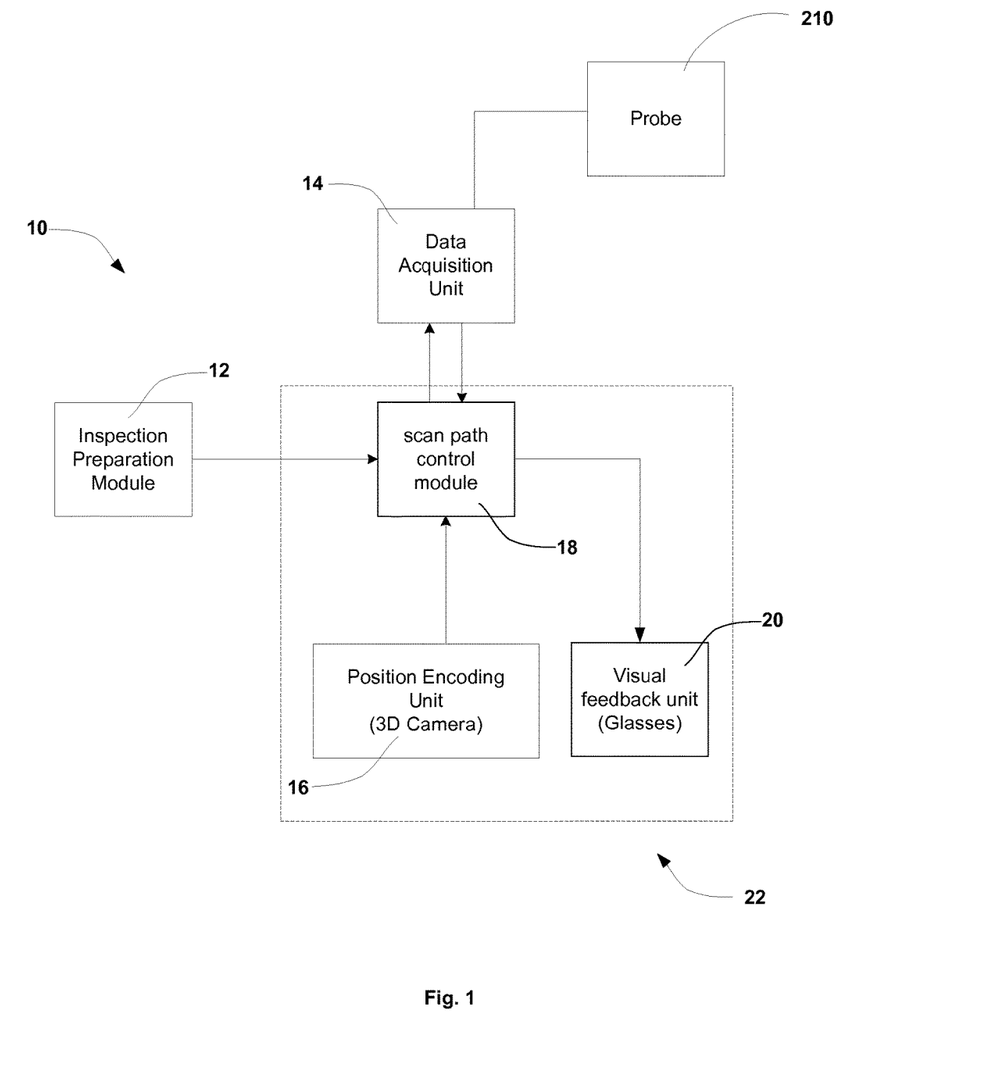
FIG. 1 is a schematic diagram showing the presently disclosed phased array system with the visual guide to assist a manual NDT inspection.
Figure 2:
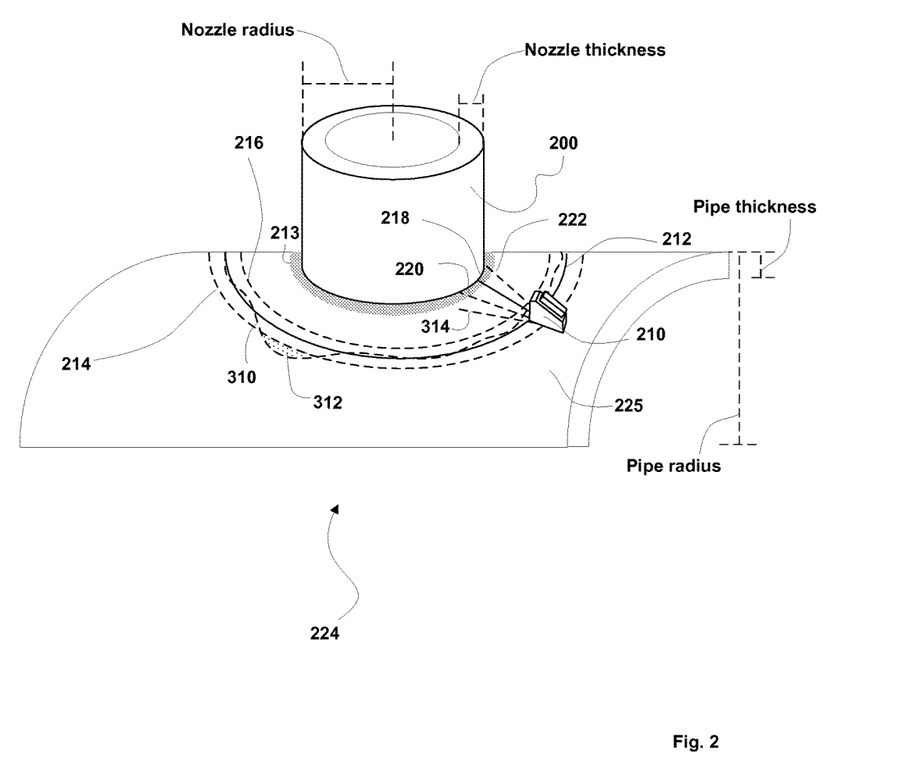
FIG. 2 is a schematic view showing a scan plan representation on theoretical part, including tolerances and a sample inspection with positioning error/variation from the scan plan.
Figure 3:
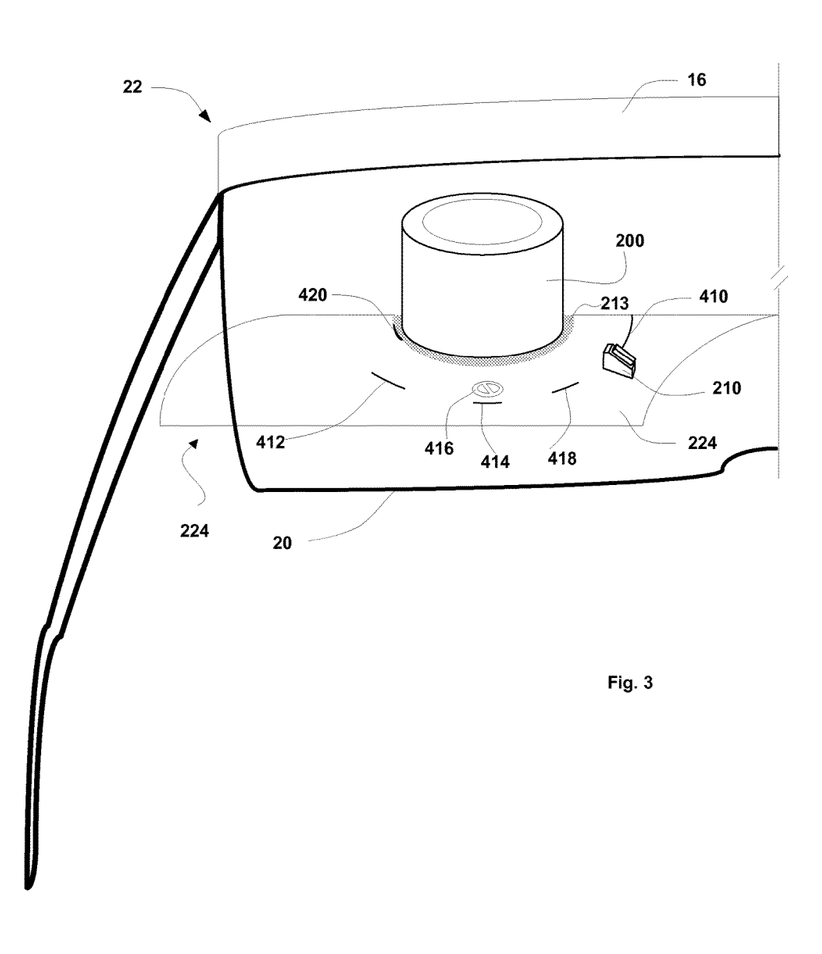
FIG. 3 is a schematic view of the visual guide unit showing the assembly of the 3D camera used as the position encoding unit and the visual feedback glasses.

Referring to FIG. 1, the presently disclosed PA system 10 with visual guide 22 comprises a phased array probe 210, a data acquisition unit 14, an inspection preparation module 12, a position encoding unit 16, a scan path control module 18 and a visual feedback unit 20. Probe 210 and data acquisition unit 14 are all existing elements of a conventional phased array system and communicate information, such as inspection signals and operational commands, among each other. Added to the conventional PA system is a visual guide unit 22 (Details are shown in FIGS. 2 and 3) which is an assembly of a scan path control module 18, position encoding unit 16 and visual feedback unit 20.

Still referring to FIG. 1, scan path control module 18 is configured to perform the following functions:
  receiving inspection plan from inspection preparation module 12,
  updating data acquisition unit 14 with the correct configuration,
  retrieving position and orientation of the part and probe from position encoding unit 16;
  validating probe position and beam orientation with respect to tolerances,
  calculating beam steering modification to program the data acquisition unit 14 in order to meet beam orientation tolerances,
  preparing information to be displayed by the visual feedback unit 20.

The inspection is first prepared by inspection preparation module 12 with a few simple geometric definitions of the test object such as diameters and thicknesses of the pipe and nozzle, and their geometric relation to one another. Using the information, an existing automated wizard is used to provide configuration information regarding a desirable path to scan the weld in order to have full coverage. The configuration information also includes operational parameters such as the beam formation to use, which part of the signal is meaningful (gating), what scan line to follow and the number of passes that are necessary to have a full coverage. Acquisition unit 14 of the PA system is configured according to the parameters above and is then ready to inspect.

The position encoding unit 16 used in the preferred embodiment is a stereoscopic 3D camera, which can locate the position and orientation of its targets in space. Targets are in a standard 3D camera system, some of whose reflective patterns can be recognized by the camera unit to enable tracking them. To calibrate 3D camera 16, for example, the test object position is tracked using a fixed target placed at a known position on the object, then the probe's target position and orientation is tracked in relation to the target fixed on the part. This allows visual feedback unit 20 to show the position and orientation of the probe on the real part and to locate it in a theoretical (virtual) part in order to make calculations and apply different tolerance conditions (shown in FIG. 2).

Continuing with FIG. 1 and assisted by referring to FIG. 2, visual guide unit 22 also embodies a pair of visual feedback unit 20, preferably employed in the form similar to that of "augmented reality glasses". Augmented reality glasses exist in the market and are partially see-through and partially a screen that can display computer generated images related to what is really seen through the glasses.

One of the novel aspects of the present disclosure is to configure a visual feedback unit in such a way to display part of the configuration information, such as the desired scanning path generated from the inspection preparation module 12, to allow wearers or inspectors to see through to observe where the probe's location is, and to employ an encoding unit (3D camera 16) to correlate the probe location in relationship to the desired scanning path.

Referring to FIG. 2 for an exemplary use of the presently disclosed guide system for inspecting a weld line 213 joining a first pipe 225 with a second pipe 200. Pipe 225 and pipe 200 together comprise a nozzle (later also referred as a test object or part) 224. In order to use the presently disclosed guide system, a plurality of geometric parameters pertaining to inspection preparation module 12 is needed. These geometric parameters include nozzle radius, nozzle thickness, pipe radius, pipe thickness, etc. Based on these parameters module 12 calculates an inspection plan scan line 212. It should be noted that this step of preparation of the scan line is also used by existing PA manual inspections, and it also can be optionally done by manual calculations, which is not the scope of the present invention. The present disclosure deals with the challenge of how to accurately and efficiently follow the scan line at a planned beam orientation 218 as shown in FIG. 2. FIG. 2 also shows scan line tolerances 214 and 216 and planned beam orientation tolerances 220 and 222.

It should be noted that the calculation of the scan plan is used but is not one of the objectives of the present disclosure. The present disclosure deals with a novel guide unit (22) to make sure the probe is following the calculated scan plan.

Continuing with FIG. 2, without the usage of the presently disclosed scan guide system, weld line 213 could be inspected with a wrong inspection line 310 which is outside of scan line tolerances 214 and 216 producing an invalid position area 312. It also shows probe 210 could be operated at a wrong beam orientation angle 314 which is outside planned tolerances 220 and 222. The glasses are firstly calibrated to the operational parameters above with the input as to where the nozzle is positioned relative to fixed target (s). Once the calibration is done the guide system can then provide guide to the user tracing the scan line to follow directly on the part through the Referenced Feedback glasses.

Continuing with FIGS. 2 and 3, a sample inspection is shown. The user does its inspection along wrong inspection line 310. Doing so, he moves probe 210 outside of scan line tolerances 214 and 216. It creates invalid position area 312 that can be seen in visual feedback unit 20 by the fact that part of line 412 of the inspection plan scan line 212 has not been removed, thus that area is considered as not inspected and was not stored by scan path control module 18. Later during the scan, a coupling problem happens and is seen in visual feedback unit (glasses) 20 as coupling error symbol 416. Part of line 414 of inspection plan scan line 212 in that region is still visible. A bit further in the inspection, wrong beam orientation angle 314 goes outside planned beam orientation angle tolerances 220 and 222. As before, part of line 418 has not been removed from inspection plan scan line 212. As the inspection progress, the user can see remaining scan line 410 on part 224 to guide the rest of the inspection. When the user sees that parts of line 412, 414 or 418 have not been removed he can go back to finish a proper inspection of these sections.

The two units 16 and 20 are preferably built into an integral assembly so that the physical position of visual feedback unit 20 in relation to position encoding unit 16 is known. There is a mechanical coupling (not shown) between two units 16 and 20 providing mechanical attachment between the two. This also serves the purpose of avoiding the need to track the units' physical locations separately.

Referring now collectively to FIGS. 2 and 3, as the inspection continues, the user is informed of the bad position of the probe, the lack of coupling fluid and the found flaw or defect position, which appears visually on the part of glasses 20 with the information fed by the control module 18. If the probe capability permits it, the system compensates for small positioning errors by modifying the beam formation to alleviate the error. FIG. 3 illustrates an example of visual guide provided during an inspection of weld line 213 guided by reference feedback glasses 20. Visual guide unit 22 assembly has two functions. First function is to track probe 210 position and orientation using position encoding unit 16. Second function is to display information, using visual feedback unit (glasses) 20, such as a coupling error symbol 416, a data value indication 420, a remaining scan line 410 as well as sections of line 412, 414 or 418, which need to be re-inspected as there was some problem during the inspection (See examples of problems given in FIG. 5).

Figure 4:
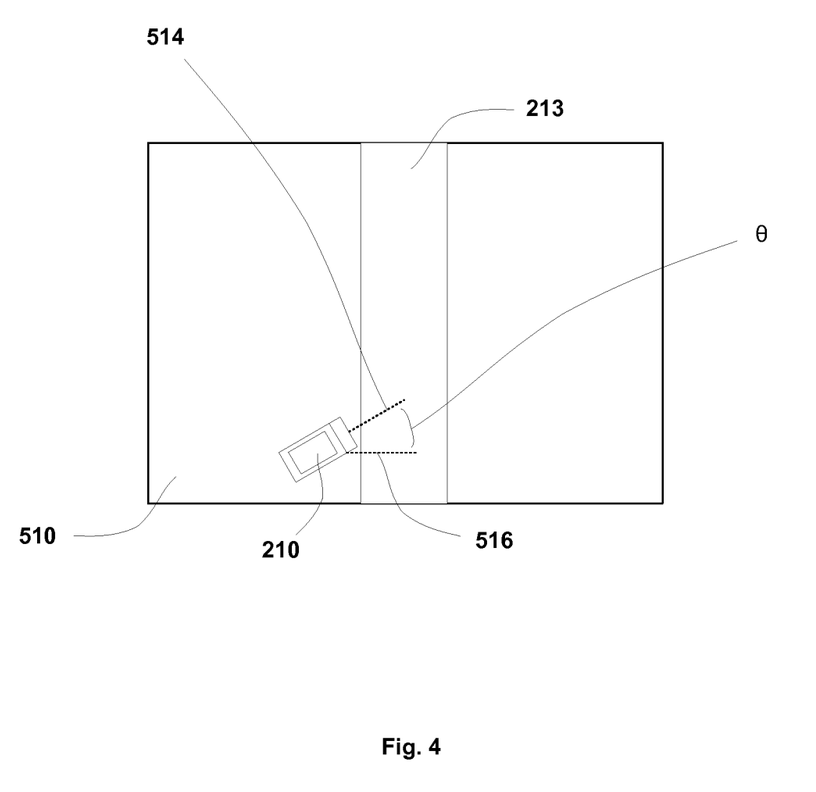
FIG. 4 is a schematic view showing the automatic beam steering adjustment assisted by the visual guide unit.

Referring now to FIG. 4, which illustrates the dynamic beam orientation correction on a simple plane part 510 using probe 210. Similar to the probe's location and trajectory detected by encoding unit 16 (3D camera), the probe's orientation angle is also sensed and provided to control module 18 by encoding unit 16. Uncorrected beam orientation angle 514 is corrected by θ steering angle, which is calculated by scan path control module 18 and then communicated to data acquisition unit 14, to get corrected beam orientation angle 516 which is perpendicular to weld 512.

Figure 5:
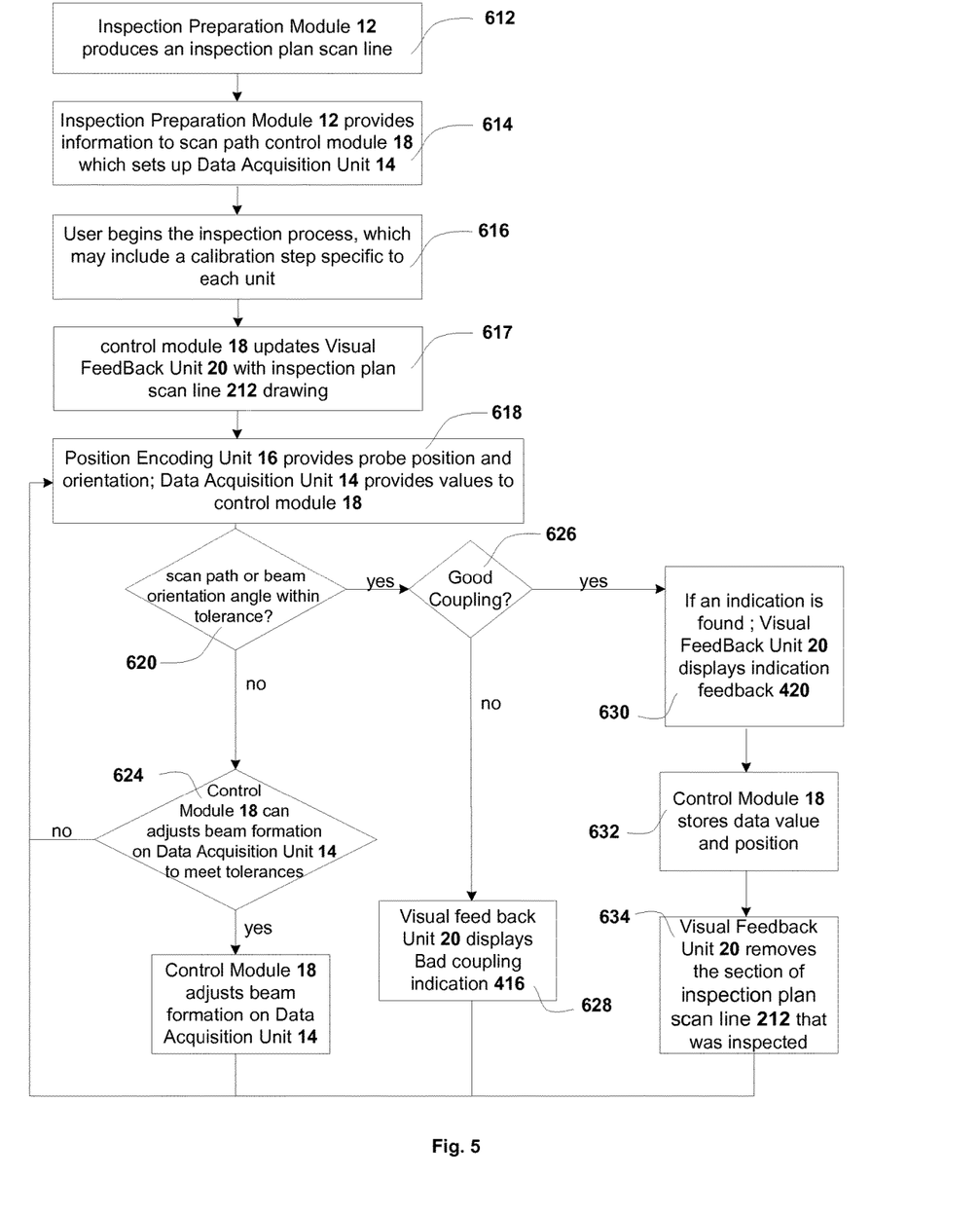
FIG. 5 is a flow chart detailing the steps in providing the visual guide to the PA scanning process.

Reference is now made to FIG. 5. In step 612 the inspection method begins with the creation of a predetermined inspection plan by inspection preparation module 12. The plan is based on pipe 225 and pipe 200's dimensions provided by the user which are: nozzle radius, nozzle thickness, pipe radius, pipe thickness. In step 614 inspection preparation module 12 provides information to scan path module 18 which sets up data acquisition unit 14 with calculated information including beam formation, gates for every beam, scan pattern(s), etc.

In step 616 the user does the calibration of the position and orientation of inspection target (weld line 213) in relation to position encoding unit 16. To have a good match of the measured position of probe 210 to weld line 213, the user must place targets on 224 and on probe 210, and then hold the position of probe 210 at a known position of part 224 at zero degree around pipe 200 with probe 210 facing the nozzle. That way the position of part 224 in the virtual space can be calculated and used as reference to display feedback information.

Once calibrated, the position of probe 210 relative to weld line 213 and the position of referenced feedback glasses 22 relative to weld line 213 are known to the system. This enables visual feedback unit 20 to display inspection plan scan line 212 onto part 224. At this state, the user can now begin the inspection, following inspection plan scan line 212 which will disappear step by step as the acquisition of valid inspection data is in progress (Also see FIG. 3).

In step 617 scan path control module 18 updates visual feedback unit 20 with inspection plan scan line 212 drawing to be followed by the user.

In step 618 position encoding unit 16 and data acquisition unit 14 provide position and data values to scan path control module 18. The data values and positions are matched together and then evaluated in the following steps.

In step 620 position requirements validation is done by scan path control module 18. There are two tolerances to be respected. First, scan line tolerances 214 and 216 restrict probe 210 position relative to inspection plan scan line 212. Next, planned beam orientation tolerances 220 and 222 restrict the rotation of probe 210 relative to planned beam orientation angle 218 at that position. If probe 210's path does not match the tolerances, scan path control module 18 attempts to adjust the beam formation to match them (step 624). Depending on the deviation from the tolerance and equipment used to do the inspection, a correct beam formation may not be found leaving the area uninspected. FIG. 4 illustrates the dynamic steering correction on simple plane part 510 using matrix phased array probe. Uncorrected beam orientation angle 514 is corrected by θ steering angle to get corrected beam orientation angle 516 which is then perpendicular to weld 512. The process then returns to step 618 to get the next acquisition point.

It should be noted that if beam orientation angle is not able to be adjusted by step 624, the warning sign from step 620 should direct the operator to readjust how the probe is held to correct the probe's orientation.

In step 626 a coupling check is done by control module 18 to verify probe 210's correct ultrasonic coupling with part 224. If a bad coupling is detected, visual feedback unit 20 displays coupling error symbol 416 on part 224 (step 628) and the process returns to step 618 to get the next acquisition point.

In step 630 visual feedback unit 20 displays data value indication 420 (in FIG. 3) which is suspected as a flaw or defect at its real position on part 224. User interprets and further determines the severity of the issue from the measurement of the phased array system. In step 632 scan path control module 18 stores the data value and its position. In step 634 visual feedback unit 20 removes the section of inspection plan scan line 212 that was inspected and the process returns to step 618 to get the next acquisition point.

It should be noted that data acquisition unit 14 of type that's normally used by ultrasound phased array system is herein used in this embodiment as an exemplary case of applying the presently disclosed method and apparatus. The framework and teaching shown in the present disclosure can be readily applied to different NDT technologies such as eddy current, bond testing, etc., and such application to other types of inspection technologies should all be covered by the scope of the present disclosure. Data acquisition unit 14 can also be the same and/or share the same unit with the phased array system.

It should also be noted that scan path controller 18 can be also implemented in the form of a series of executable routines, executed by a digital processor, such as that of the same process as the existing phased array system that the controller is integrated to. On the other hand, controller 18 can be on a stand-alone processor as deemed fit for different designs. The framework and teaching shown in the present disclosure can be readily applied to all the variations of designs pertaining to the scan path controller.

It should be noted that 3D camera system is exemplarily used in this embodiment as position encoding unit 16 applying the presently disclosed method and apparatus. The framework and teaching shown in the present disclosure can be readily applied to different encoding technologies such as standard rotary encoders, 3D arms, magnetic encoding system, etc. and such application to other types of encoding technologies should all be covered by the scope of the present disclosure.

It should be noted that visual feedback unit 20 which takes the form of glasses are herein used in this embodiment as an exemplary case of applying the presently disclosed method and apparatus. The framework and teaching shown in the present disclosure can be readily applied to different visual guide technologies such as Laser Projection System, on screen, etc; and such application to other types of visual guide technologies should all be covered by the scope of the present disclosure.

It should be noted that position encoding unit 16 and visual feedback unit 20 are herein used in this embodiment as an integrated unit, referenced feedback glasses 22. The framework and teaching shown in the present disclosure can be readily applied to separate units, position encoding unit 16 which tracks visual feedback unit 20 that then displays the feedback information relative to its position. It should also be covered by the scope of the present disclosure.

It should be noted that in this embodiment, in step 624, uncorrected beam orientation angle 514 is corrected by θ steering angle to get electronically corrected beam orientation angle 516 which is then perpendicular to weld 512. The teaching shown in the present disclosure can be readily applied to other beam forming change that allows retaining proper acoustic coverage of the inspected zone. It should also be covered by the scope of the present disclosure.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A non-destructive inspection and testing system configured for inspecting or measuring a test object according to a predetermined inspection plan during an inspection operation conducted by an operator, the system comprising:
   a probe configured to emit ultrasonic energy, the ultrasonic energy is configured to have at least one beam with electronically steered ultrasonic beam angle, to the test object and receive corresponding response signals from the test object,
   a data acquisition unit configured to control the beam angles and to receive response signals from the probe,
   a data processor, which further comprises
      an inspection preparation module configured to receive geometric information regarding the test object and to provide the predetermined inspection plan, and
      an inspection guide control module configured to receive the predetermined inspection plan,
   a position encoding unit sensing and providing the probe's sensed position during the inspection operation to the control module,
   a visual feedback viewing unit configured to display information including the predetermined inspection plan to the operator, and to allow the operator to visualize and hence to position the probe according to the predetermined inspection plan, wherein the control module is configured to validate the probe's sensed position in respect to the predetermined inspection plan and to validate if the corresponding steered beam angle is within a predetermined beam orientation tolerance, and if not, to calculate a corrected steering angle based on the probe's sensed position, and communicate to the data acquisition unit to automatically correct the beam angle with the corrected steering angle.

2. The inspection and testing system of claim 1, wherein the inspection preparation module is executed by the data processor.

3. The inspection and testing system of claim 1, wherein the inspection preparation module includes off-line or manual computation.

4. The inspection and testing system of claim 1, wherein the control module is further configured to receive inspection tolerance of the deviation from the predetermined inspection plan and to validate the sensed probe position in respect to the tolerance.

5. The inspection and testing system of claim 4, wherein the control module is further configured to instruct the visual feedback unit to display a warning of when the sensed probe position is out of the inspection tolerance.

6. The inspection and testing system of claim 4, wherein the control module is further configured to instruct the visual feedback viewing unit to display a portion of the predetermined inspection plan for which the probe's position is out of the tolerance indicating the inspection has been missed.

7. The inspection and testing system of claim 4, wherein the control module is further configured to instruct the visual feedback viewing unit to erase portions of the predetermined inspection plan for which the inspection is deemed properly done.

8. The inspection and testing system of claim 1, wherein the inspection plan is a trajectory along which the probe should be moved, and the position encoding unit is configured to sense and provide real time information to the control module regarding the probe's sensed location in respect to the test object.

9. The inspection and testing system of claim 1, wherein the inspection plan is a plot of orientations according to which the probe should be positioned, and the position encoding unit is configured to sense and provide real time information to the control module regarding the probe's sensed orientations of the probe.

10. The inspection and testing system of claim 1, wherein the inspection plan includes a trajectory and a plot of orientations according to which the probe should be positioned and the position encoding unit is configured to sense and provide real time information to the control module regarding the probe's sensed positions in respect to the test object.

11. The inspection and testing system of claim 1, wherein the data acquisition module is configured to receive the inspection signals from the probe and to transmit probe setup information from the control module to the probe.

12. The inspection and testing system of claim 1, wherein the control module further includes a circuitry and/or at least one module for processing inspection data samples based on the inspection signals.

13. The inspection and testing system of claim 12, the control module is further configured to produce a warning or alert if an anomaly is found, and instruct the visual feedback viewing unit to display such warning or alert.

14. The inspection and testing system of claim 1, wherein the position encoding unit is a 3 dimensional camera.

15. The inspection and testing system of claim 1, wherein the visual feedback viewing unit is an augmented reality eyewear.

16. The inspection and testing system of claim 1, wherein the system is an ultrasonic phased array system.

17. The inspection and testing system of claim 1, wherein the system is an ultrasonic inspection instrument.

18. The inspection and testing system of claim 1, wherein the system is an eddy current inspection device.

19. The inspection and testing system of claim 1, wherein the system is an X-ray analytical device.

20. A method of conducting an inspection on a test object with a predetermined inspection plan by using an ultrasonic inspection device, the method comprising the steps of:
   coupling the device with an ultrasonic probe which is configured to beam energy at predetermined steering angles, and the probe is configured to be movable according to the inspection plan on the test object,
   providing an inspection plan by receiving a geometric definition regarding the test object, providing the predetermined inspection plan on the test object to a control module,
facilitating a virtual display of the inspection plan onto a visual feedback viewing unit,
moving the probe following the virtual display of the inspection plan,
sensing sensed probe positions in real time of the inspection,
validating the sensed probe position against the inspection plan,
calculating a corrected ultrasonic steering angle based on the sensed probe positions, and electronically correcting the steering angles with the corrected steering angle if the sensed probe position is not within a predetermined tolerance of the inspection plan,
displaying information including of the step of validating on the visual feedback viewing unit.

21. The method of claim 20, wherein the visual feedback viewing unit further includes a position encoding unit.

22. The method of claim 21, wherein the step of sensing sensed probe positions is conducted by the position encoding unit, and the sensed positions are provided to the control module which performs the step of validating and further providing alert information to be displayed on the visual feedback viewing unit.

23. The method of claim 21, wherein the inspection plan includes a trajectory line of probe locations and a plot of probe orientations and the step of validating includes validating both the sensed probe locations and probe orientations.

* * * * *